US005693669A

United States Patent [19]
Herrmann et al.

[11] Patent Number: 5,693,669
[45] Date of Patent: Dec. 2, 1997

[54] TILIDINE DIHYDROGEN ORTHOPHOSPHATE, METHOD OF PREPARING IT AND PHARMACEUTICAL PREPARATION CONTAINING IT

[75] Inventors: Wolfgang Herrmann, Stockmattenweg; Armin Knapp, Grubstrasse; Hans Klausmann, Muldenstrasse, all of Germany

[73] Assignee: Gödecke Aktiengesellschaft, Berlin, Germany

[21] Appl. No.: 424,370

[22] PCT Filed: Oct. 25, 1993

[86] PCT No.: PCT/EP93/02954

§ 371 Date: May 26, 1995

§ 102(e) Date: May 26, 1995

[87] PCT Pub. No.: WO94/10129

PCT Pub. Date: May 11, 1994

[30] Foreign Application Priority Data

Oct. 26, 1992 [DE] Germany .................. 42 36 074.9

[51] Int. Cl.$^6$ .................. A61K 31/215; C07C 211/40
[52] U.S. Cl. .................. 514/538; 560/48
[58] Field of Search .................. 556/13; 560/48; 514/538

[56] References Cited

U.S. PATENT DOCUMENTS

| | | | |
|---|---|---|---|
| 3,557,127 | 1/1971 | Satzinger et al. | 260/294.3 |
| 4,800,083 | 1/1989 | Hom et al. | 424/457 |
| 4,933,438 | 6/1990 | Bodor | 536/6.4 |
| 5,478,577 | 12/1995 | Sackler et al. | 424/489 |

*Primary Examiner*—Jose G. Dees
*Assistant Examiner*—Laura Cross
*Attorney, Agent, or Firm*—Elizabeth M. Anderson

[57] ABSTRACT

The instant invention is a tilidine salt, tilidine dihydrogen orthophosphate, which owing to its surprising stability, is particularly suitable for use in the preparation of solid, in particular delayed-action, drugs in tablet, pill or capsule form.

6 Claims, 1 Drawing Sheet

TILIDINE DIHYDROGEN ORTHOPHOSPHATE, METHOD OF PREPARING IT AND PHARMACEUTICAL PREPARATION CONTAINING IT

This is a 371 of PCT/EP93/02954 filed Oct. 25, 1993.

BACKGROUND OF THE INVENTION

The instant invention is for the new salt, tilidine dihydrogen orthophosphate, a process for its preparation and pharmaceutical compositions containing it. Tilidine [(±)-ethyl trans-2-dimethylamino-1-phenyl-3-cyclohexene-trans-1-carboxylate)] is a commercially available analgesic which is enterally resorbed very quickly and is especially suitable for the treatment of very severe pains. For galenical compositions, salts of the basic active material are used since the base as such does not have sufficient stability over a comparatively long period of time. Until now for reasons of stability, even with the use of salts, it has not been possible to develop solid pharmaceutical forms, such as tablets or suppositories.

Only the hydrochloride semihydrate (DE-PS 1 518 959 and 1 793 571 [U.S. Pat. No. 3,557,127]) has, in practice, proved to be useful as a salt for stable liquid compositions. It is commercially available in the form of a solution or of a portioned suspension in soft gelatin capsules under the trademark Valoron N. Because of its outstanding properties in combatting pain, Valoron N has become one of the leading analgesics in Germany. All endeavors to make available useful solid pharmaceutical forms of the active material tilidine have been unsuccessful because of the stability problems. There is a need for a useable solid galenical form of tilidine because only such a solid formulation can provide a controllable release of tilidine. Tilidine acts for a relatively short period of time and a uniform treatment of pain for a comparatively long period of time, with a single dose of active material is needed. Normal release, such as is provided by liquid compositions, is problematical. A sustained form would be a very great advance in the field of analgesics and especially where a uniform, high level of active material over a long period of time is required. Such a form would be useful in combatting chronic and severe painful conditions such as in the treatment of cancer and in the treatment of burns.

SUMMARY OF THE INVENTION

The present invention provides a tilidine salt which is stable in solid and sustained pharmaceutical compositions, especially in tablets, coated tablets, and suppositories. A process for the production of solid and sustained pharmaceutical compositions of this new salt is included.

The new salt is tilidine dihydrogen orthophosphate.

The invention covers a solid, sustained-release pharmaceutical composition comprising:

(a) tilidine dihydrogen orthophosphate, and (b) conventional solid pharmaceutical adjuvants.

The pharmaceutical composition can also contain one or more agents for sustained release.

The composition is selected from: a tablet, a coated tablet, a capsule, a suppository, or a granulate.

Further, the invention involves a process for the preparations of tilidine dihydrogen orthophosphate comprising:

(a) dissolving tilidine base in isopropanol containing 4–10% by weight water, and warming to from 30°–50° C., (b) stirring while adding a solution of 80–90% orthophosphoric acid over a period of about 3 hours while adding seed crystals continuously, (c) cooling slowly to room temperature while stirring, and (d) centrifuging and washing the product from (c) above.

A more preferred process for producing tilidine dihydrogen phosphate comprises:

(a) dissolving tilidine base in isopropanol containing 4–10% by weight water, and warming to 35°–45° C., (b) stirring while adding a solution of 85–88% orthophosphoric acid over a period of 3 hours while adding seed crystals continuously, (c) cooling the product of step (b) above overnight to room temperature with stirring, and (d) centrifuging the crystals from step (c) above and washing twice with 10 L of 94% isopropanol.

DETAILED DESCRIPTION

Figure 1:
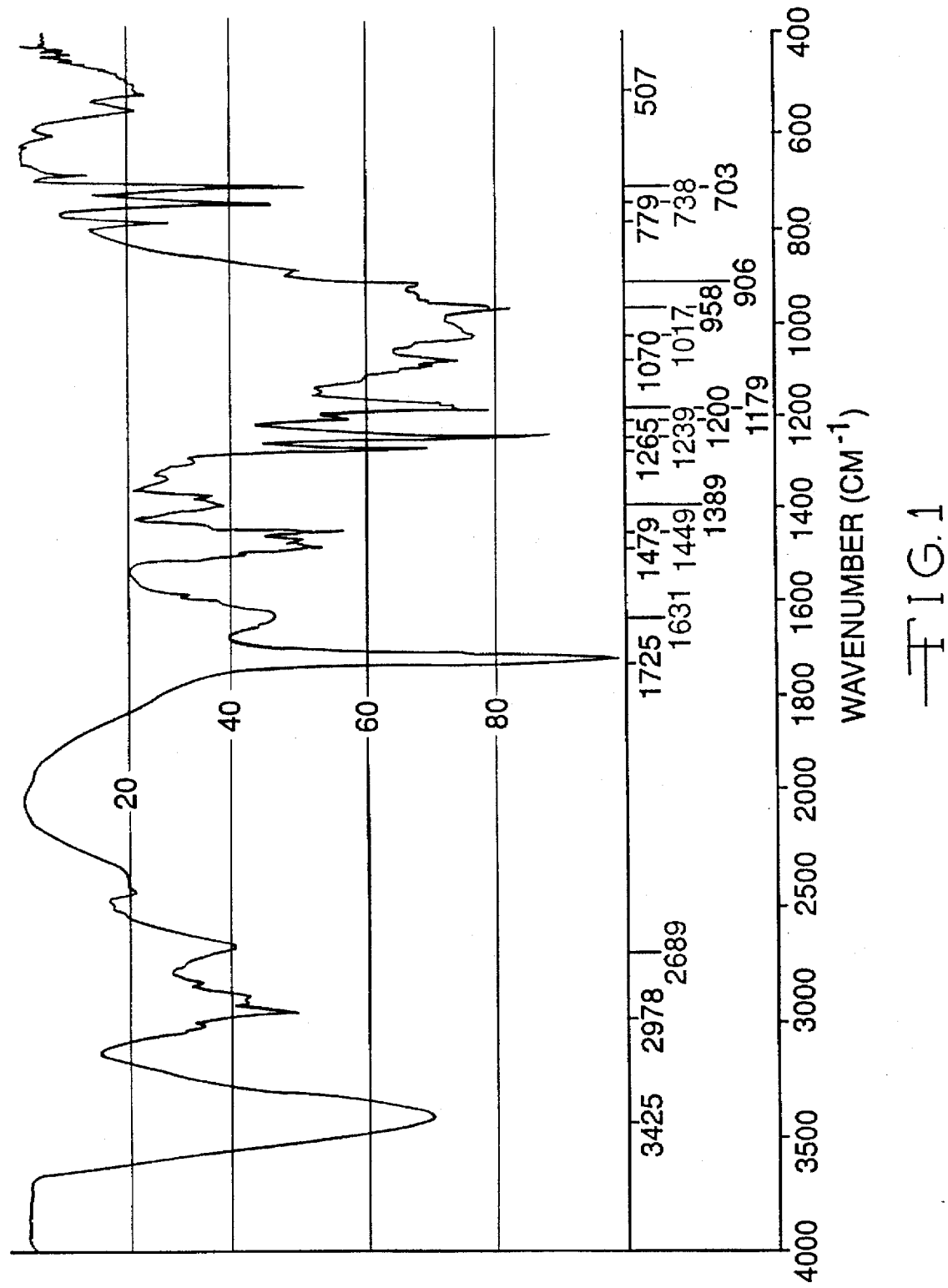
FIG. 1 is the IR spectrum of the salt of the invention.

Surprisingly, we have now found that tilidine dihydrogen orthophosphate has outstanding stability and is the only salt suitable for the production of solid pharmaceutical compositions. In solid form, in combination with solid adjuvants, it undergoes practically no decomposition. Further, the new salt has surprising pharmaceutical-technological properties which are superior to the properties of other tilidine salts, such as, tilidine hydrogen sulfate or tilidine hydrogen fumarate. It can be prepared without special requirements as to the climate in the production rooms and the corrosion protection of the apparatus and tools used. Granulates, tablets, and suppositories can be produced which are storage stable not only chemically but also physically over a very long period of time.

In DE-1 923 619, (U.S. Pat. No. 3,649,628) it is mentioned in passing that basically substituted cyclohexenes can form salts with a number of organic and inorganic acids, inter alia also with phosphoric acid which can possibly be considered for working up to give pharmaceutical compositions. No phosphate is described and especially not tilidine dihydrogen orthophosphate. Moreover, the above-mentioned stability problems and especially those of tilidine are not described. Hitherto, there has been no indication in the literature regarding the difficulties concerning the storage stability of this active material or of the technical problems when it is worked up to give solid pharmaceutical compositions. Therefore, one had no reason or no indication that precisely tilidine dihydrogen orthophosphate would be especially suitable for solving the above problems.

In addition, it has been found that the methods used in the production of the phosphate is critical and must to be carried out under very special conditions if a crystalline product of high purity is to be obtained. The salt formation is started with 80–90%, preferred 85–88% orthophosphoric acid, which is dissolved in an amount of water containing isopropanol (water content 4–10% by weight, preferred 6%) which is suitable for a complete solution. This solution is combined at a temperature of 30°–50° C., preferred 40°±5° C. with a solution of 0.8–1.2 mol, preferred 1 mol of tilidine base in isopropanol of the above given water content under stirring in about stoichiometric amounts and the suspension obtained is slowly (over several hours) cooled under stirring. After washing with the isopropanol tilidine dihydrogen orthophosphate of 99.5% purity in a yield of more than 90% is obtained. Both the water content and reaction temperature parameters are important. At temperatures below 35° C. and with water products with impurities of the solvents and bad crystallization behavior, products which are not completely dryable and which retain persistent isopropanol are produced.

Therefore, the present invention provides tilidine dihydrogen orthophosphate and a process for the preparation thereof. The present invention also provides a solid and especially a sustained-release solid galenical pharmaceutical composition consisting of conventional solid pharmaceutical adjuvants, as well as, if desired, releasing agents, which is characterized by tilidine dihydrogen orthophosphate as the active material, and the production thereof.

For the production of sustained-release solid pharmaceutical compositions containing tilidine, all conventional processes for sustained-release which do not have a negative influence on the stability of the active material on the basis of their composition. A sustained-release tablet prepared by a melt process according to EP-PS 0 043 254 (U.S. Pat. No. 4,483,847) is especially useful. Generally, as sustained-release agents any sparingly soluble material can be used, for example lipid or lipoid substance such as stearic acid and especially hydrogenated castor oil (Cutina HR) (DE-A 1 617 657 [3,487,138] and U.S. Pat. No. 4,123,753) or hydrophilic polymers, which, as swelling materials, delay the liberation of the active material (see J. Pharm. Sci., p. 974/1966). For the objective control of the rate of liberation the process according to EP-PS 0 068 446 (U.S. Pat. No. 4,608,248) can also be used through the rate of liberation of the active material from an active material composition made sustained by means of sparingly-soluble substance is adjusted by the viscosity of an added hydrophilic polymer, for example methyl cellulose or carboxymethyl cellulose, since the speed of liberation increases with increasing viscosity.

The surprising superiority of the dihydrogen orthophosphate is demonstrated by comparison with:

(a) tilidine hydrochloride semihydrate
(b) tilidine hydrogen fumarate
(c) tilidine hydrogen sulphate and
(d) tilidine dihydrogen orthophosphate.

In each case the compound was triturated with naloxone hydrochloride dihydrate and conventional adjuvants. Naloxone hydrochloride semihydrate is an effective morphine antagonist which commercially available tilidine compositions contain. After storage for 28 days at 60° C., distinct differences are shown in the four salts: whereas mixtures a) to c) were substantially discolored, mixtures of d) showed no change of color and thus, no decomposition phenomena.

In a further experiment, three different salts of tilidine were, in each case, worked up with naloxone hydrochloride dihydrate, hydrogenated castor oil, lactose, hydroxyethyl cellulose, stearic acid, tablettose and magnesium stearate to give melt granulate tablets. With tilidine hydrogen fumarate, event in the case of the production of the melt granulate, there was shown a strong green coloration. The tablets with tilidine hydrochloride semihydrate showed orange-grey discolorations after only two days storage in brown glass containers at 22° C. On the other hand, the tablets with tilidine dihydrogen orthophosphate showed no discolorations under the same conditions even after storage for six months.

In the product samples, the new dihydrogen orthophosphate also proved to be extremely good with regard to the working up properties.

It was not hygroscopic, did not react with metallic materials and was inert towards electrostatic charging. At a relative humidity of 63%, the hydrochloride semihydrate took up considerable amounts of water and acted corrosively on tools which were not specially protected against corrosion. In the case of a relative atmospheric humidity of 58%, the sulphuric acid salt already took up water and exceeded the hydrochloride semihydrate in its aggressive corrosion behavior. The would cause imprecise weighed amounts and the partial demixing of the adjuvant and active materials.

The following examples are for the purpose of illustrating the present invention; they are not intended to limit its scope in any way.

EXAMPLE 1

Preparation of tilidine dihydrogen orthophosphate: 27.091 kg (99.10 mol) tilidine base were dissolved in 99 L of 94% isopropanol (6% water) with warming to about 40° C. (±5° C.). While stirring, a solution of 11.54 kg of 85–88% orthophosphoric acid (corresponding to 9.844 kg=100.46 mol of 100%, acid) was added thereto at 40° C. over 3 hours. For improved crystallization, seed crystals were continuously added. The suspension was slowly cooled overnight to ambient temperature, while stirring. The crystals were centrifuged off and washed twice with 10 L of 94% isopropanol. The white salt obtained was dried at 50 to 60° C. Yield: 33.89 kg (92.09% of theory). The salt had an analytical purity (HPLC) of 99.5%, mp 137.0° C. Molecular weight: 371.37. For IR spectrum of the salt see in FIG. 1.

EXAMPLE 2

Retarded (sustained release) tablets containing 120 mg of tilidine dihydrogen orthophosphate: 960 g tilidine dihydrogen orthophosphate, prepared according to Example 1, were premixed with 70.4 g naloxone hydrochloride dihydrate, 740 g lactose and 700 g hydrogenated castor oil and then slowly heated with continuing mixing to a product temperature of 83° C. The resultant melt mass was removed from the mixing vessel and passed through a sieve of 2.5-mm size. After cooling to ambient temperature, the product was passed through a further sieve of 1-mm mesh size. Subsequently, 273.6 g ammonia methacrylate copolymer, 32 g magnesium stearate and 24 g silicon dioxide were sieved and uniformly mixed with granulate. The mixture was then pressed with an eccentric press to provide round, slightly domed tablets of 10-mm diameter, 11-mm dome radius and 350-mg nominal weight. The tablets have the following composition:

| | |
|---|---|
| tilidine dihydrogen orthophosphate | 120.0 mg |
| naloxone hydrochloride dihydrate USP | 8.8 mg |
| lactose | 92.5 mg |
| hydrogenated castor oil | 87.5 mg |
| ammonia methacrylate copolymer | 34.2 mg |
| magnesium stearate | 4.0 mg |
| silicon dioxide | 3.0 mg |

The following product properties were determined for the tablets obtained:
weight average value: 351 mg, minimum 340 mg, maximum 363 mg, $S_{rel}$ 1.8%
breaking strength: average value 82N, minimum 64N, maximum 90N, $S_{rel}$ 8.4%
friability: 0.23%
breakdown: more than 3 hours.

EXAMPLE 3

Suppositories containing 59.95 mg tilidine dihydrogen orthophosphate: 9700 g hard fat with a hydroxyl number 40–50 (Witepsol W 35 [R]) or an alternative hard fat with a hydroxyl number of up to 2 (massa estarinum R 299) was melted at 45° C. in a heatable vessel equipped with a stirrer until completely clear. After cooling to 36° to 38° C., 300 g tilidine dihydrogen orthophosphate were dispersed in the molten fat base with the help of an Ultra-Turrax (R) mixer. The product temperature was thereby maintained at 36° to 38° C., possibly with cooling of the mantle of the vessel. The melt ready for casting was then poured out in a shaping, filling and closing machine into suppository blisters made of triple-laminate film. The casting temperature at the dosing plant was maintained at 37° C. During the casting, the temperature of the vessel was 37° C. The dosage amount per filling station was 2.0 g±5%. The suppositories were cooled during transport through a cooling tunnel in which a temperature of 20 to ° C. prevailed and thereby solidified. The blisters were subsequently heat-sealed and stamped out. In this way, up to 9000 suppositories were produced per hour. The batch used in the present example provided 4850 suppositories each containing 59.93 mg tilidine dihydrogen orthophosphate (corresponding to 50 mg tilidine hydrochloride).

We claim:

1. The compound tilidine dihydrogen orthophosphate.

2. A solid, sustained-release pharmaceutical composition comprising:
   (a) tilidine dihydrogen orthophosphate, and
   (b) conventional solid pharmaceutical adjuvants.

3. A composition according to claim 2 containing one or more sustained-release agents.

4. The composition according to claim 2, selected from a tablet, a coated tablet, a capsule, a suppository, or a granulate.

5. A process for the preparations of tilidine dihydrogen orthophosphate comprising:
   (a) dissolving tilidine base in isopropanol containing 4–10% by weight, water, and warming to from 30°–50° C.,
   (b) stirring while adding a solution of 80–90% orthophosphoric acid over a period of about 3 hours while adding seed crystals continuously,
   (c) cooling slowly to room temperature while stirring, and
   (d) centrifuging and wash the product from (c) above.

6. A process according to claim 5 comprising:
   (a) dissolving tilidine base in isopropanol containing 4–10% by weight water and warming to 35°–45° C.,
   (b) stirring while adding a solution of 85–88% orthophosphoric acid over a period of 3 hours while adding seed crystals continuously,
   (c) cooling the product of step (b) above overnight to room temperature with stirring, and
   (d) centrifuging the crystals from step (a) above and washing twice with 10 L of 94% isopropanol.

* * * * *